United States Patent [19]

Graf et al.

[11] Patent Number: 5,919,887

[45] Date of Patent: *Jul. 6, 1999

[54] DECOLORATION OF POLYISOCYANATES CONTAINING ISOCYANURATE AND DIRETDIONE GROUPS

[75] Inventors: Hermann Graf, Mutterstadt; Ernst Deuker; Stefan Wolff, both of Ludwigshafen; Ludwig Schuster, Limburgerhof; Serge Wack, Ludwigshafen; Richard Hardt, Frankenthal, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/858,352

[22] Filed: May 19, 1997

Related U.S. Application Data

[63] Continuation of application No. 08/574,569, Dec. 15, 1995, abandoned, which is a continuation of application No. 08/425,668, Apr. 17, 1995, abandoned, which is a continuation of application No. 08/054,173, Apr. 30, 1993, abandoned.

[30] Foreign Application Priority Data

May 13, 1992 [DE] Germany .............................. 42 15 746

[51] Int. Cl.$^6$ .......... C08G 18/74; C07D 229/00; C01B 13/00
[52] U.S. Cl. .................. 528/45; 528/67; 528/73; 252/186.1; 540/202
[58] Field of Search ............................ 252/186.1, 186.21; 544/221, 222; 540/202; 528/45, 67, 73

[56] References Cited

U.S. PATENT DOCUMENTS

| 984,221 | 2/1911 | Hornbostel ........................... 252/186.1 |
| 3,086,534 | 4/1963 | Gorter et al. ........................ 252/186.1 |
| 4,935,391 | 6/1990 | Caropreso et al. ...................... 501/146 |
| 4,994,541 | 2/1991 | Dell et al. ................................. 528/51 |
| 5,143,994 | 9/1992 | Laas et al. ................................ 528/45 |
| 5,208,334 | 5/1993 | Potter et al. ............................ 544/193 |
| 5,237,058 | 8/1993 | Laas et al. .............................. 540/202 |

*Primary Examiner*—Joseph D. Anthony
*Attorney, Agent, or Firm*—Fernando A. Borrego

[57] ABSTRACT

A process for decoloring polyisocyanates containing isocyanurate and uretdione groups comprises treating the demonomerized polyisocyanates containing isocyanurate and uretdione groups with oxygen.

9 Claims, No Drawings

DECOLORATION OF POLYISOCYANATES CONTAINING ISOCYANURATE AND DIRETDIONE GROUPS

This application is a continuation of application Ser. No. 08/574,569, filed Dec. 15, 1995 now abandoned, which is a continuation of application Ser. No. 08/425,668, filed Apr. 17, 1995 now abandoned, which is a continuation of application Ser. No. 08/054,173, filed Apr. 30, 1993, now abandoned.

BACKGROUND OF THE INVENTION

The present invention relates to a process for decoloring polyisocyanates containing isocyanurate and uretdione groups.

The isocyanate components employed in high-quality one- and two-component polyurethane paints having high light and weathering resistance are, in particular, polyisocyanate mixtures containing isocyanurate and uretdione groups.

These products are preferably prepared by catalytic oligomerization of aliphatic and/or cycloaliphatic diisocyanates, eg. 1-isocyanato-3,3,5-trimethyl-5-isocyanatomethylcyclohexane (IPDI) or 1,6-diisocyanatohexane (HDI).

Examples of catalysts which can be employed are hydroxides or organic salts of weak acids with tetraalkylammonium groups, hydroxides or organic salts of weak acids with hydroxyalkylammonium groups, or alkali metal salts or tin, zinc or lead salts of alkylcarboxylic acids.

The aliphatic and/or cycloaliphatic diisocyanates are reacted in the presence of a catalyst, if desired with use of solvents and/or auxiliaries, until the desired conversion has been achieved. The reaction is then terminated by deactivating the catalyst, and the excess monomeric diisocyanate is removed by distillation. Depending on the catalyst type and reaction temperature used, polyisocyanates containing various proportions of isocyanurate and uretdione groups are obtained.

The products prepared in this way are mostly clear, but have a certain yellow coloration depending on the catalyst type, the diisocyanate quality, the reaction temperature and the reaction procedure.

However, products having a low color index are desired for the preparation of high-quality polyurethane paints. A number of processes are known from the prior art for reducing the color index of such products. Thus, DE-A-38 06 276 proposes reducing the carbon dioxide content of the HDI employed as monomer to less than 20 ppm before the oligomerization by degassing under reduced pressure and subsequently blowing nitrogen through the HDI, and employing quaternary ammonium hydroxides as the oligomerization catalyst. However, the carbon dioxide removal step is technically very complex.

EP-A-0 339 396 proposes using quaternary ammonium fluorides as the trimerization catalyst. Although this process tolerates a higher carbon dioxide content, the catalyst employed must, however, be chemically deactivated. The resultant compounds remain in the product and may result in applicational problems on further processing. A further way of preparing low-color-index polyisocyanates containing isocyanurate groups is the addition, proposed in EP-A-0 336 205, of polyester-diols to the starting diisocyanate. This allows the amount of catalyst employed to be reduced, but the resultant products are still relatively highly colored.

According to EP-A-0 377 177, aliphatic diisocyanates are oligomerized in the presence of phosphines as catalyst, and, after termination of the oligomerization, some of the unreacted diisocyanate is removed by distillation and some is converted into urethane by addition of alcohol. The reaction product is subsequently treated with peroxides. Although the peroxide treatment significantly reduces the color index of the oligomerization product, the use of peroxides is, however, associated with problems. Thus, peroxides are frequently difficult to handle industrially. Peroxides which are safer to handle are usually supplied in solution, but the dibutyl phthalate frequently used as solvent causes applicational problems in the preparation of paints.

It is an object of the present invention to provide a simple process for the effective decoloration of polyisocyanates containing isocyanurate and uretdione groups which avoids the disadvantages of the prior art.

We have found that, surprisingly, this object is achieved by treating the demonomerized polyisocyanates containing isocyanurate and uretdione groups with oxygen.

SUMMARY OF THE INVENTION

The present invention accordingly provides a process for decoloring polyisocyanates containing isocyanurate and uretdione groups which comprises treating the demonomerized polyisocyanates containing isocyanurate and uretdione groups with oxygen.

DESCRIPTION OF THE PREFERRED EMBODIMENTS

The polyisocyanates containing isocyanurate and uretdione groups are prepared by catalytic oligomerization, which is known per se, of aliphatic and/or cycloaliphatic diisocyanates.

The known aliphatic and/or cycloaliphatic diisocyanates can be employed; for processing as paint raw materials, IPDI and/or HDI, in particular, are used. The oligomerization is generally carried out at from 0 to 100° C. while passing an inert gas, preferably nitrogen, through the mixture. Catalyst which can be used are all catalysts which are known for the oligomerization of aliphatic and/or cycloaliphatic diisocyanates, for example those mentioned at the outset. In order to reduce the amount of catalyst, it is possible to add a small amount, up to about 1% by weight, based on the diisocyanate, of a diol, in particular a polyester-diol, to the diisocyanate before the oligomerization.

The diisocyanate is then warmed to the reaction temperature with stirring, and the catalyst is added slowly. For better handling, the catalyst can be dissolved in a solvent. Examples of suitable solvents are alcohols, in particular diols, ketones, ethers and esters.

When the desired conversion has been reached, the reaction is terminated by deactivating the catalyst, for example by adding a catalyst poison or by thermal decomposition. The reaction mixture is subsequently freed from the excess monomeric diisocyanate, preferably by distillation, for example by means of a thin-film evaporator.

The reaction product obtained has a pronounced yellow coloration.

In order to reduce the color index, the polyisocyanates containing isocyanurate and uretdione groups are then treated with oxygen.

This is carried most simply by passing oxygen through the polyisocyanates containing isocyanurate and uretdione groups.

Either pure oxygen or air can be employed. In addition, the gas stream may contain up to 20% by volume, based on the oxygen, of ozone. It has also proven advantageous to irradiate the reaction products with UV light at the same time as the oxygen treatment.

The reaction temperature should be from 85 to 170° C., preferably from 90 to 115° C., if air is used, from 80 to 150° C., preferably from 90 to 110° C., if oxygen is used and from 5 to 170° C., preferably from 25 to 100° C., if ozone is admixed.

It is advantageous to work in the preferred moderate temperature range, since decoloration proceeds very slowly at lower temperatures and partial re-cleaving of the oligomers can occur at higher temperatures. The oxygen treatment according to the invention is carried out at atmospheric pressure or a slight superatmospheric pressure of up to about 200 kPa. The reaction times are generally, depending on the amount of oxygen fed in, from 0.5 to 6 hours in the case of treatment with air, from 0.3 to 3.0 hours in the case of treatment with oxygen and from 5 minutes to 30 minutes if ozone is added to the oxygen stream. The optimum reaction time can easily be determined by a few preliminary experiments.

It was surprising that decoloration of the polyisocyanates containing isocyanurate and uretdione groups was possible by this very simple method. A person skilled in the art would have expected that oxygen treatment at the temperatures used would result in a deepening in the color, especially as it is known, for example from JP-A-157 657, that the presence of oxygen during the oligomerization of aliphatic diisocyanates gives strongly colored products.

The novel process makes it possible to decolor polyisocyanates containing isocyanurate and uretdione groups without the need to modify the oligomerization process. It is also possible to further decolor oligomerization products having low color indices.

EXAMPLES

Example 1

700 g of an HDI modified with isocyanurate groups and having an NCO content of 22.3%, a residual HDI content of 0.08% by weight and a color index of 63 Hazen, measured in accordance with DIN/ISO 6271, were introduced into a reactor fitted with stirrer and gas-inlet tube, and were warmed to 160° C. Air was passed through the HDI for 50 minutes at this temperature at a rate of 5.0 l/h. The reaction mixture was then cooled to room temperature.

After the treatment, the oligomerized HDI had an NCO content of 22.2%, a residual HDI content of 0.68% by weight and a color index of 5 Hazen, measured in accordance with DIN/ISO 6271.

Example 2

700 g of an HDI modified with isocyanurate groups and having an NCO content of 22.3%, a residual HDI content of 3.0% by weight and a color index of 100 Hazen, measured in accordance with DIN/ISO 6271, were introduced into a reactor as described in Example 1 and warmed to from 158 to 162° C. Air was then passed through the HDI for 40 minutes at a rate of 5.0 l/h. After cooling, the color index was 35 Hazen, measured in accordance with DIN/ISO 6271.

Example 3

700 g of an HDI modified with isocyanurate groups and having an NCO content of 22.3%, a residual HDI content of 2.8% by weight and a color index of 35 Hazen, measured in accordance with DIN/ISO 6271, were introduced into a reactor as described in Example 1 and warmed to 131° C. Air was then passed through the HDI for 40 minutes at a rate of 30 l/h. After cooling, the color index was 15 Hazen, measured in accordance with DIN/ISO 6271.

Example 4

50 g of an HDI modified with isocyanurate groups were introduced into a reactor as described in Example 1 and warmed to 120° C. Air was passed through the HDI for 25 minutes at this temperature at a rate of 3.0 l/h. The color index dropped from 14 to 2 Hazen, measured in accordance with DIN/ISO 6271.

Example 5

The procedure was similar to that of Example 4, but the reaction temperature was kept at 100° C. The color index of the HDI dropped from 16 to 11 Hazen, measured in accordance with DIN/ISO 6271.

Example 6

The procedure was similar to that of Example 4, but the reaction temperature was 90° C. and the reaction time was 95 minutes. The color index of the HDI dropped from 31 to 17 Hazen, measured in accordance with DIN/ISO 6271.

Example 7

20 $m^3$/h of air were passed into a continuous stirred reactor charged with 400 kg/h of an HDI modified with isocyanurate groups and having a residual HDI content of 4% and a color index of 80 Hazen, measured in accordance with DIN/ISO 6271, in such a manner that the liquid was flushed-through vigorously. The mean residence time of the HDI was 2.8 hours, and the reaction temperature was 120° C. The color index of the product leaving the reactor was 30 Hazen, measured in accordance with DIN/ISO 6271.

Example 8

The procedure was similar to that of Example 7, but the mean residence time was 2.5 hours and the reaction temperature was 110° C. The color index of the HDI dropped from 60 to 25 Hazen, measured in accordance with DIN/ISO 6271.

Example 9

The procedure was similar to that of Example 7, but the residual HDI content of the HDI modified with isocyanurate groups was 2.0% by weight. The color index dropped from 80 to 40 Hazen, measured in accordance with DIN/ISO 6271.

Example 10

20 $m^3$/h of air were passed into a continuous stirred reactor charged with 360 kg/h of an HDI modified with isocyanurate groups and having an NCO content of 22.2%, a residual HDI content of 0.08% by weight and a color index of 60 Hazen, measured in accordance with DIN/ISO 6271, in such a manner that the liquid was flushed-through vigorously. The mean residence time of the HDI was 5.8 hours, and the reaction temperature was 95° C. The color index of the product leaving the reactor was 15 Hazen, measured in accordance with DIN/ISO 6271.

Example 11

The procedure was similar to that of Example 10, but with a product feed of 370 kg/h, a mean residence time of 5.6 hours and a reaction temperature of 90° C. The color index of the HDI dropped from 60 to 25 Hazen, measured in accordance with DIN/ISO 6271.

Example 12

330 g of an HDI modified with isocyanurate groups and having an NCO content of 22.4%, a residual HDI content of 0.08% by weight and a color index of 35 Hazen, measured in accordance with DIN/ISO 6271, were introduced into a 500 ml reactor fitted with gas-dispersion stirrer having a maximum speed of 2,000 rpm, and were warmed to 90° C. An ozone/oxygen mixture containing 250 g of ozone per $m^3$ of oxygen was passed in via the stirrer for 7 minutes at this temperature at a rate of 50 l/h. The color index of HDI after the treatment was less than 5 Hazen, measured in accordance with DIN/ISO 6271; the other product parameters remained unchanged.

Example 13

The procedure was similar to that of Example 12, but the HDI modified with isocyanurate groups had an NCO content of 22.3%, a residual HDI content of 3.0% by weight and a color index of 40 Hazen, measured in accordance with DIN/ISO 6271, and the reaction time was 10 minutes. The color index of the HDI after the treatment was 5 Hazen, measured in accordance with DIN/ISO 6271; the other product parameters remained unchanged.

Example 14

3.1 kg of HDI modified with isocyanurate groups and to which 0.03% by weight of benzoyl chloride had been added were warmed to 70° C. in a 3.4 l reactor fitted with the gas-dispersion stirrer described in Example 12. An ozone/oxygen mixture containing 240 g of ozone per $m^3$ of oxygen was passed in via the stirrer for 15 minutes at this temperature at a rate of 50 l/h. The color index of the HDI dropped from 40 to 6 Hazen, measured in accordance with DIN/ISO 6271.

Example 15

The procedure was similar to that of Example 12, but the reaction temperature was 90° C., the ozone concentration was 44 g per $m^3$ of oxygen and the reaction time was 10 minutes. The color index of the HDI dropped from 50 to 6 Hazen, measured in accordance with DIN/ISO 6271.

Example 16

800 g of an HDI modified with isocyanurate groups and having an NCO content of 22.4%, a residual monomer content of 0.10% by weight and a color index of 128 Hazen, measured in accordance with DIN/ISO 6271, were introduced into a reactor fitted with gas-inlet tube and stirrer, and warmed to 90° C. 13 l/h of oxygen having a purity of 99.9% were bubbled through the gas-inlet tube into the liquid at this temperature. The color index of the HDI was 86 Hazen after a reaction time of 30 minutes, 62 Hazen after 60 minutes and 37 Hazen after 210 minutes. The other product parameters remained unchanged.

Example 17

The procedure was similar to that of Example 16, but the HDI modified with isocyanurate groups had a color index of 94 Hazen, measured in accordance with DIN/ISO 6271, and the reaction temperature was 105° C. The color index of the HDI was 41 Hazen after 30 minutes, 29 Hazen after 60 minutes, 21 Hazen after 90 minutes and 8 Hazen after 120 minutes, measured in accordance with DIN/ISO 6271.

Example 18

30 g of an HDI modified with isocyanurate groups and having an NCO content of 23.3%, a residual monomer content of 3.2% by weight and a color index of 51 Hazen were warmed to 161° C. in the presence of air. Table 1 shows the dependence of the color index on the reaction time.

| Time (min) | 0 | 10 | 15 | 20 | 30 | 50 | 70 |
|---|---|---|---|---|---|---|---|
| Color index (Hazen) | 51 | 20 | 11 | 7 | 14 | 34 | 51 |

The HDI had the following product parameters after completion of the experiment: NCO content 22.4%, residual monomer content 3.1% by weight.

We claim:

1. A process for decoloring polyisocyanates containing isocyanurate and uretdione groups, which comprises terminating an oligomerization reaction of at least one diisocyanate wherein the resulting reaction product is a mixture comprised of (i) polyisocyanates containing isocyanurate and uretdione groups and (ii) excess diisocyanate;

removing the (ii) excess diisocyanate from the reaction product to produce demonomerized polyisocyanates containing isocyanurate and uretdione groups; and treating the demonomerized polyisocyanates containing isocyanurate and uretdione groups with a gaseous oxidizing stream selected from the group consisting of air, an oxygen/ozone mixture containing up to 20 percent by volume ozone based on the amount of oxygen, and pure oxygen;

wherein when the oxidizing stream is air, the step of treating the demonomerized polyisocyanate is carried out at from 85 to 170° C., when the oxidizing stream is pure oxygen, the step of treating the demonomerized polyisocyanate is carried out at from 80 to 150° C., and when the oxidizing stream is oxygen/ozone mixture, the step of treating the demonomerized polyisocyanate is carried out at from 5 to 170° C.

2. A process as claimed in claim 1, wherein the at least one diisocyanate is an aliphatic and/or cycloaliphatic diisocyanate.

3. A process as claimed in claim 2, wherein the at least one diisocyanate is 1,6-hexamethylene diisocyanate.

4. A process as claimed in claim 1, wherein the gaseous oxidizing stream comprises the oxygen/ozone mixture containing up to 20 percent by volume of ozone.

5. A process as claimed in claim 4, wherein the step of treating the demonomerized polyisocyanate is carried out at from 15 to 100° C.

6. A process as claimed in claim 1, 2 or 3, wherein the gaseous oxidizing stream comprises air.

7. A process as claimed in claim 6, wherein the step of treating the demonomerized polyisocyanate is carried out with air at from 90 to 115° C.

8. A process as claimed in claim 1 or 2 or 3, wherein the gaseous oxidizing stream comprises pure oxygen.

9. A process as claimed in claim 8, wherein the step of treating the demonomerized polyisocyanate is carried out with pure oxygen at from 90 to 110° C.

* * * * *